(12) United States Patent
Wei et al.

(10) Patent No.: US 9,090,471 B2
(45) Date of Patent: Jul. 28, 2015

(54) METHOD FOR PRODUCING FLUORAPATITE AND ITS APPLICATION

(75) Inventors: Shicheng Wei, Beijing (CN); Jie Wei, Beijing (CN); Xiaochen Liu, Beijing (CN); Chengjie Wang, Beijing (CN); Yifei Zhang, Beijing (CN)

(73) Assignee: Peking University, Haidian District (CN)

( * ) Notice: Subject to any disclaimer, the term of this patent is extended or adjusted under 35 U.S.C. 154(b) by 849 days.

(21) Appl. No.: 13/256,617

(22) PCT Filed: Sep. 2, 2010

(86) PCT No.: PCT/CN2010/001336
§ 371 (c)(1),
(2), (4) Date: Feb. 1, 2012

(87) PCT Pub. No.: WO2011/160265
PCT Pub. Date: Dec. 29, 2011

(65) Prior Publication Data
US 2012/0128566 A1      May 24, 2012

(30) Foreign Application Priority Data

Jun. 22, 2010 (CN) .......................... 2010 1 0205839
Jun. 30, 2010 (CN) .......................... 2010 1 0213917

(51) Int. Cl.
*C01B 25/10* (2006.01)
*C01B 25/455* (2006.01)
*A61K 6/06* (2006.01)

(52) U.S. Cl.
CPC ............. *C01B 25/455* (2013.01); *A61K 6/0643* (2013.01)

(58) Field of Classification Search
CPC ....................................................... C01B 25/10
USPC ....................................................... 423/301
See application file for complete search history.

(56) References Cited

U.S. PATENT DOCUMENTS

| | | | |
|---|---|---|---|
| 4,855,118 A | 8/1989 | Ichinose et al. | |
| 4,959,104 A | 9/1990 | Iino et al. | |

FOREIGN PATENT DOCUMENTS

| | | | |
|---|---|---|---|
| CN | 1475436 A | 2/2004 | |
| JP | 5085710 A | 6/1993 | |

*Primary Examiner* — Edward Johnson
(74) *Attorney, Agent, or Firm* — Kilpatrick Townsend & Stockton LLP (57) ABSTRACT

This application provides a novel method for producing a tetracalcium phosphate-based fluorapatite. Also provided is a method of using the fluorapatite for repairing enamel defects.

20 Claims, 6 Drawing Sheets

METHOD FOR PRODUCING FLUORAPATITE AND ITS APPLICATION

FIELD OF THE INVENTION

The present invention relates to the field of biomaterials for dental repairing utilization. More particularly, the invention relates to a method of producing fluorapatite for repairing tooth enamel defects caused by caries.

BACKGROUND OF THE INVENTION

Dental caries (decayed tooth) is a progressive disease to hard tissues of teeth, which is caused by a cooperative function of multiple factors in oral cavity. It is a major common oral disease with features of high incidence and wide distribution. Dental caries, along with cancer and cardiovascular diseases, are called the three major diseases of human being by World Health Organization. As reported by a survey of national oral epidemiology, the incidence of dental caries for the residents in China is 50% and the incidence of dental caries for deciduous tooth is 80%. According to the statistical result from the survey, the total amount of decayed teeth is up to 2 billion in China, 90% of which have never been treated. As estimated by a recent survey in America, nearly 80% of children and 90% of adults have been bothered by dental caries. As the development of economy and continuous improvement of living conditions, the dietary structure of modern people has also been changed to a great extent to contain more fine, sticky, and soft food and be rich in sugar, which causes dental caries easily. Dental caries, which has become the most epidemical bacterial infection disease, threats people's oral health severely. The defects in tooth tissues has a negative impact on oral functions such as chewing, language, and etc., and on aesthetics as they happen to the front teeth.

Microbes (e.g. streptococcus mutans) can form plagues on the surface of tooth enamel in an oral cavity, and the plagues, by producing acid and etching and demineralizing tooth enamel repeatingly, cause damage to tooth enamel and further to dentin. Dental caries, depending on the decayed extent, can be divided into three phases clinically, including shallow, moderate, and deep caries. In the phase of shallow caries, decay is only limited to enamel, and causes no obvious cavity. In the phase of moderate caries, decay reaches the superficial layer of dentin, and causes obvious cavities. In the phase of deep caries, decay extends to the deep layer of dentin, and big and deep cavities or cavities with small openings but wider damages in the deep layer appear. Dental caries can cause irreversible damage to the tooth enamel/dentin and loss of tooth function, and can also cause diseases to dental pulp and periapical tissue of root canal. The purposes of caries treatment are to stop the pathologic process of dental caries, to prevent its continuous progression, and to restore the inherent shape and function of teeth. Up to now, with respect to the existed caries, clinicians still use the method comprising steps of destructively grinding and removing decayed tooth tissues (including enamel and/or dentin), and using oral repairing material (including resin, metal, or ceramic) for filling and repairing (shown in the following Figures). These methods are unable to restore the original structure of tooth tissue, and may even cause potential problems of resulting in secondary caries and harming the biomechanical performance of tooth.

The greater damage caused by progression of dental caries can be stopped by preventing caries from happening on the layer of tooth enamel and providing nondestructive treatment on the early stage of tooth enamel caries. Despite owning an ability of remineralization, a tooth can not repair itself from a substantial damage due to its specific structure. Thus, for the tooth substantially damaged, a filling therapy is the most widely used method and has a better effect. The shape and function of a tooth can be restored using filling therapies, inlays, or artificial crowns according to ranges and sizes of tooth defects. Up to now, with respect to the existed caries, even to slight caries, clinicians still use the method comprising the steps of destructively grinding and removing decayed tooth tissues (including enamel and/or dentin), preparing a cavity with a suitable shape, and using biologically inactive oral repairing material such as resin, dental metal such as silver amalgam, or ceramic material for filling and repairing. Although favorable effects of restoring the shape and function of tooth tissues can be achieved by this repairing method in a short term, there will be secondary caries or breaks and shedding of the inlay in a long term due to contraction and aging of the material. However, with respect to the early enamel caries which are not suitable for the preparation of a cavity, or to some caries which do not possess resistance and retention, it is not appropriate to use the above material for filling.

Fluorapatite was first found in tooth by Heneh et al. Fluorapatite has the same crystal structure as hydroxyapatite with only a replacement of OH by F—. As known, fluorine has an electronegativity value of 4, the highest in all elements. Therefore, the bond strength between F— and Ca in fluorapatite is far greater than the bond strength between OH— and Ca in hydroxyapatite, which is one of the main reasons for the stability of fluorapatite. Since a variation in composition leads to a variation in performance of such material, domestic and international biomaterial scientists pay great attention to and proceed an intensive study on this issue. Because group F is smaller than group OH, fluorapatite has more compact crystal structure and thus smaller lattice constant than hydroxyapatite. Due to the more compact structure, fluorapatite has a lower solubility. Because of the significant meaning of this feature in clinical applications, fluorapatite can be used as a replacement material for bone and tooth. When fluorapatite is used as a nondegradable replacement material for hard tissues with high-load bearing structures, especially when fluorapatite is used as a dental material, the microrelease of fluorine ion can stimulate the growing of bone, and can also resist against erosion of body fluid and saliva to the material so as to shorten the healing period for bone. All these indicate great advantages of the biomaterial of fluorapatite.

DISCLOSURE OF THE INVENTION

The present invention is intended to provide a material for repairing tooth enamel defects caused by caries, which can be generated at the original location (where enamel defects caused by caries appear), so as to be used for repairing enamel defects caused by caries, especially for repairing severe tooth enamel defects (deep caries).

A method for producing fluorapatite is provided in the present invention, characterized in comprising the steps of mixing tetracalcium phosphate, calcium hydrogen phosphate, and sodium fluoride to form a mixture and then adding the mixture into water, or mixing tetracalcium phosphate and ammonium fluoride to form a mixture and then adding the mixture into a phosphoric acid/water solution; blending the above two sets of materials respectively to form cement-like substances; and solidifying the cement-like substances at a temperature of 35° C. to 38° C. and a moisture of 100% for 1-3 days.

Hydration reactions to synthesize fluorapatite can be represented as following formulas:

tetracalcium phosphate+calcium hydrogen phosphate+ sodium fluoride-fluorapatite $$2Ca_4(PO_4)_2O+2CaHPO_4+2NaF \longrightarrow Ca_{10}(PO_4)_6F_2$$

or tetracalcium phosphate+phosphoric acid+ammonium fluoride-fluorapatite $$5Ca_4(PO_4)_2O+2H_3PO_4+4NH_4F \longrightarrow 2Ca_{10}(PO_4)_6F_2$$

Tetracalcium phosphate with a particle diameter of 1 to 20 μm and calcium hydrogen phosphate with a particle diameter of 1 to 20 μm are mixed evenly by a star-shape ball mill, blent with sodium fluoride, and then added to water. The resultant cement-like substance was filled into the cavities of tooth enamel defects caused by caries. After 1~3 days of solidification in human physiological conditions, fluorapatite is formed, so as to repair the tooth enamel defects caused by caries.

Or, in the present invention, the cement-like substance formed from tetracalcium phosphate ($Ca_4(PO_4)_2O$), a phosphoric acid/water solution ($H_3PO_4$), and ammonium fluoride was filled into the cavities of tooth enamel defects (deep caries) or small enamel cavities on the tooth surface. After 1~3 days of solidification in human physiological conditions, fluorapatite is formed, so as to repair the enamel defects.

In the present invention, materials including tetracalcium phosphate, calcium hydrogen phosphate, and etc. are blent to form the cement-like substance which can be filled into the places where enamel defects caused by caries occur as a material for repairing tooth enamel defects caused by caries. Solidified body of the cement-like substance is combined with the original enamel closely. In other words, the resultant fluorapatite is combined with the surface of enamel defects closely (through certain interface chemical reactions).

The advantages of the present invention are listed below:

The resultant fluorapatite has a similar chemical composition with tooth enamel, thus, repairing material can be combined with natural enamel directly. The material powder and water are mixed to form a cement-like substance (having plasticity), and the cement-like substance finally forms fluorapatite through a hydration reaction of the material. In this way, fluorapatite with a controllable structure (the cement-like substance can be figured to any shape according to the shape of tooth enamel defects, and can be combined with the surface of enamel defects closely) can be synthesized directly on the surface of tooth enamel defects, so as to repair tooth enamel defects caused by deep caries. On the other hand, the fluorapatite produced in the present invention has a stoichiometric amount of apatite structure, and has high chemical stability (low solubility) in a physiological condition of human body fluid. In acidic conditions (when bacteria exist) the fluorapatite releases fluorine ion slowly so as to have the ability to prevent dental caries. The direct regeneration of fluorapatite on the surface of human tooth enamel defects might be achieved by the controllable synthesis of fluorapatite, which will be a completely new method for repairing hard tissues and has revolutionary meaning to dental care and regenerative medical treatment.

BRIEF DESCRIPTION OF THE DRAWINGS

FIG. 4 is a SEM photo of the fluorapatite synthesized in the embodiment, disclosed in the present invention, of mixing tetracalcium phosphate, calcium hydrogen phosphate, sodium fluoride, and water, wherein FIG. 4(a) is a photo with a low amplification ratio (×50K), and FIG. 4(b) is a photo with a high amplification ratio (×100K);

FIG. 5 is a photo of repairing tooth enamel defects (deep caries) in the embodiment, disclosed in the present invention, of mixing tetracalcium phosphate, calcium hydrogen phosphate, sodium fluoride, and water, wherein

FIG. 10 is a SEM photo of the fluorapatite synthesized in the embodiment, disclosed in the present invention, of mixing tetracalcium phosphate, ammonium fluoride, and a phosphoric acid/water solution, wherein FIG. 10(a) is a photo with a low amplification ratio (×10,000), and FIG. 10(b) is a photo with a high amplification ratio (×30,000);

FIG. 11 is a photo of repairing tooth enamel defects (deep caries) in the embodiment, disclosed in the present invention, of mixing tetracalcium phosphate, ammonium fluoride, and a phosphoric acid/water solution, wherein

DETAILED DESCRIPTION OF THE EMBODIMENTS

In light of the drawings, the present invention is further described by Examples.

The embodiment disclosed in the present invention, characterized in mixing tetracalcium phosphate, calcium hydrogen phosphate, sodium fluoride, and water, meets the following criteria:

1. Molar ratio of tetracalcium phosphate to calcium hydrogen phosphate is 1:1
2. Molar ratio of tetracalcium phosphate to sodium fluoride is 1:1.
3. Ratio of the powder mixture of tetracalcium phosphate, calcium hydrogen phosphate, and sodium fluoride to water is 1~4 (g/mL).

Particular examples of mixing tetracalcium phosphate, calcium hydrogen phosphate, sodium fluoride, and water are provided as follows.

Example 1

Figure 1:
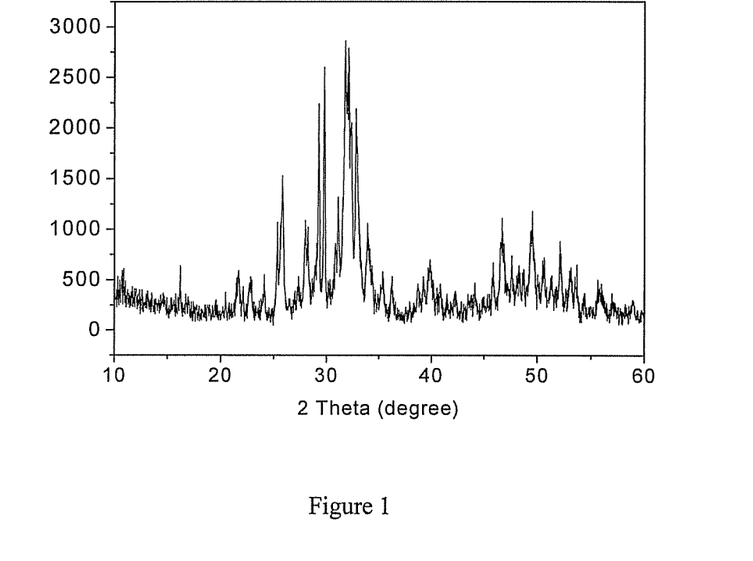
FIG. 1 is a XRD spectrum of the fluorapatite synthesized in the embodiment, disclosed in the present invention, of mixing tetracalcium phosphate, calcium hydrogen phosphate, sodium fluoride, and water.
Figure 2:
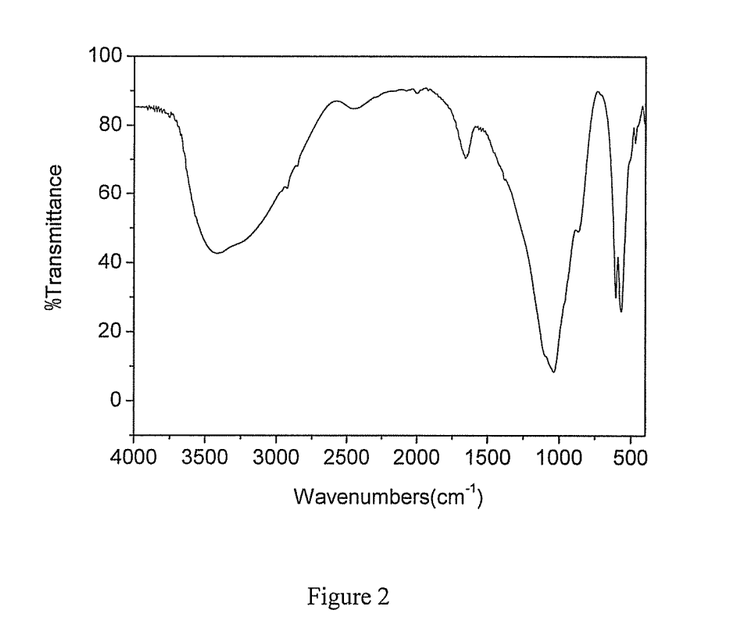
FIG. 2 is a IR spectrum of the fluorapatite synthesized in the embodiment, disclosed in the present invention, of mixing tetracalcium phosphate, calcium hydrogen phosphate, sodium fluoride, and water.
Figure 3:
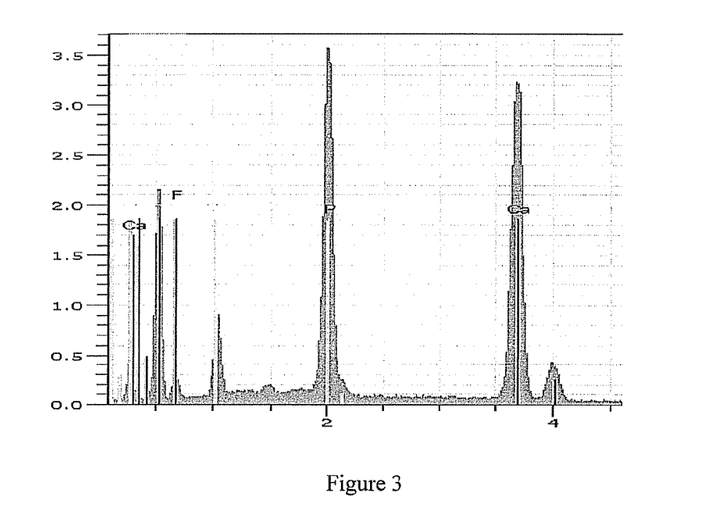
FIG. 3 is a EDS spectrum of the fluorapatite synthesized in the embodiment, disclosed in the present invention, of mixing tetracalcium phosphate, calcium hydrogen phosphate, sodium fluoride, and water.

Tetracalcium phosphate powder (2.66 g) and calcium hydrogen phosphate powder (1.36 g) were mixed evenly, then 0.4 g sodium fluoride was added into and blent with the resultant mixed powder evenly in a mixing plate. After the powder mixture of the above three materials was added into 4 mL water, the obtained mixture was blent by a key to form a cement-like substance and further to form a gel-like substance. Fluorapatite was formed after the gel-like substance was kept in an environment with a temperature of 37° C. and a moisture of 100% for 3 days. The results of XRD, IR, and EDS, which characterize the chemical structure and composition of the product, are shown in FIG. 1-3. According to the XRD spectrum, the resultant product has characteristic peaks near $2\theta=26°$, $2\theta=32°$, $2\theta=34°$, $2\theta=40°$, $2\theta=47°$, $2\theta=50°$. This result indicates that the synthesized product is fluorapatite. According to the IR spectrum, the absorption peaks for $PO_4^{3-}$ appear at 1070 $cm^{-1}$ and 950 $cm^{-1}$, and the two absorption peaks at 1432 and 1750.8 $cm^{-1}$ and the absorption peaks between 2800 $cm^{-1}$ and 3472 $cm^{-1}$ all belong to hydroxyl group of water. The vibration peak of P—O—H bond of apatite appears at 877.7 $cm^{-1}$. According to the EDS spectrum, the synthesized product comprises elements of calcium, phosphorus, and fluorine. The calculated quantitative result of the atomic molar ratio is shown as follows: the atomic molar ratio of calcium to phosphorus is 1.67 and the atomic molar ratio of calcium to fluorine is 2. These results also demonstrate that the synthesized product is fluorapatite.

Example 2

Figure 4:
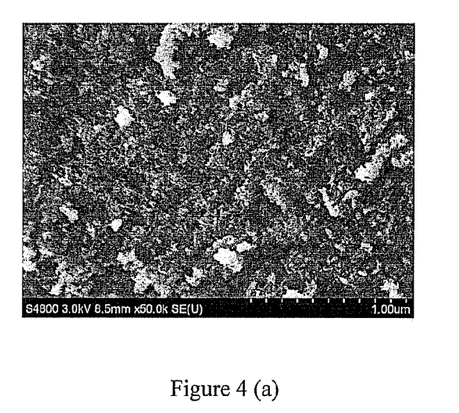
Figure 5A:
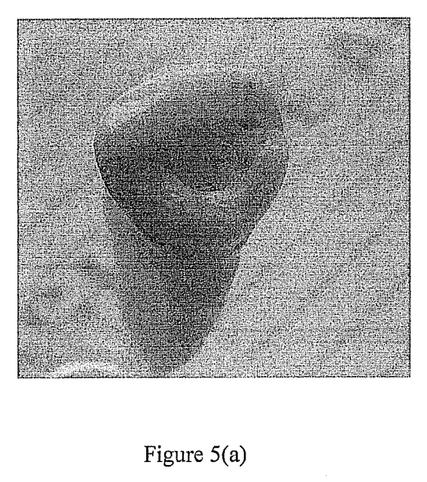
FIG. 5(a) is a photo of the tooth before repaired.
Figure 5B:
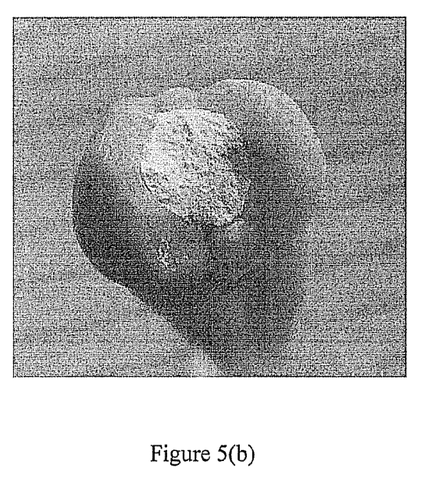
FIG. 5(b) is a photo of the tooth filled with the repairing material.
Figure 6:
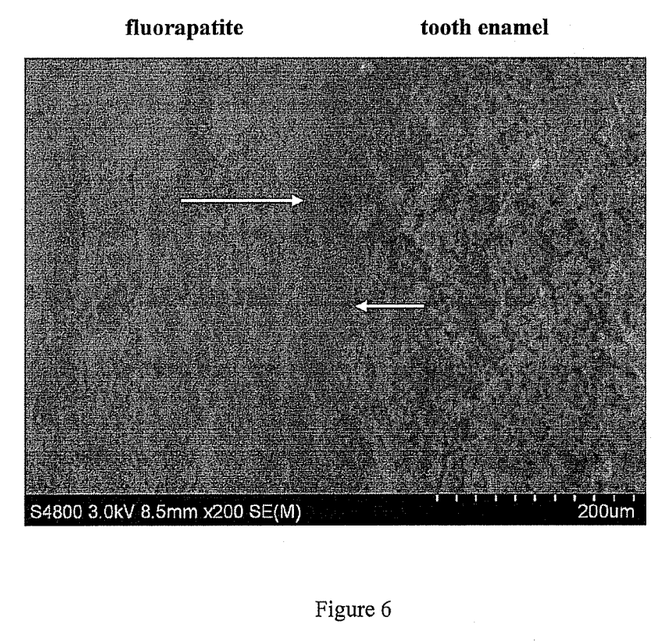
FIG. 6 is a SEM photo of repairing tooth enamel defects caused by caries with the fluorapatite synthesized in the embodiment, disclosed in the present invention, of mixing tetracalcium phosphate, ammonium fluoride, and a phosphoric acid/water solution, wherein the arrows point at the interface between fluorapatite and tooth enamel.

Tetracalcium phosphate powder (1.33 g) and calcium hydrogen phosphate powder (0.68 g) were mixed evenly, then 0.2 g sodium fluoride was added into and blent with the resultant mixed powder evenly in a mixing plate. After the powder mixture of the above three materials was added into 2 mL water, the obtained mixture was blent by a key to form a cement-like substance and further to form a gel-like substance. An experimental sample was acquired after a tooth was filled with the gel-like substance in the place where tooth enamel defects caused by caries appeared and kept in an environment with a temperature of 37° C. and a moisture of 100% for 3 days. As shown in FIG. 4, microcosmic structure of the material's surface was characterized by SEM. According to the SEM photo, fluorapatite was combined with tooth enamel closely without any obvious gap on their interface. This result also indicates that the repairing material fluorapatite has a similar composition with tooth enamel, so they can be easily combined together. The synthesized fluorapatite appeared as needle and bar like crystals that are combined together closely. The material and the combined tooth were cut through the center of the material, and the combining status of the interface between the material and the surface of tooth enamel defects was observed, as shown in FIG. 6.

Example 3

Tetracalcium phosphate powder (26.6 g) and calcium hydrogen phosphate powder (13.6 g) were mixed evenly with a star-shape ball mill. Four gram of sodium fluoride was add into water to form its solution. After the powder mixture of tetracalcium phosphate and calcium hydrogen phosphate was added into 40 mL water, the obtained mixture was blent by a key to form a cement-like substance and further to form a gel-like substance. An experimental sample was acquired after a tooth was filled with the gel-like substance in the place where tooth enamel defects caused by caries appeared and kept in an environment with a temperature ranging from 35° C. to 38° C. and a moisture of 100% for 3 days.

Another embodiment disclosed in the present invention, characterized in mixing tetracalcium phosphate, ammonium fluoride, and a phosphoric acid/water solution, meets the following criteria:
1. Molar ratio of tetracalcium phosphate to phosphoric acid is 5:2.
2. Molar ratio of tetracalcium phosphate to ammonium fluoride is 1:1.
3. Percentage concentration of the phosphoric acid solution is 20%~70%.

Particular examples of mixing tetracalcium phosphate, ammonium fluoride, and a phosphoric acid/water solution are provided as follows.

Example 4

Figure 7:
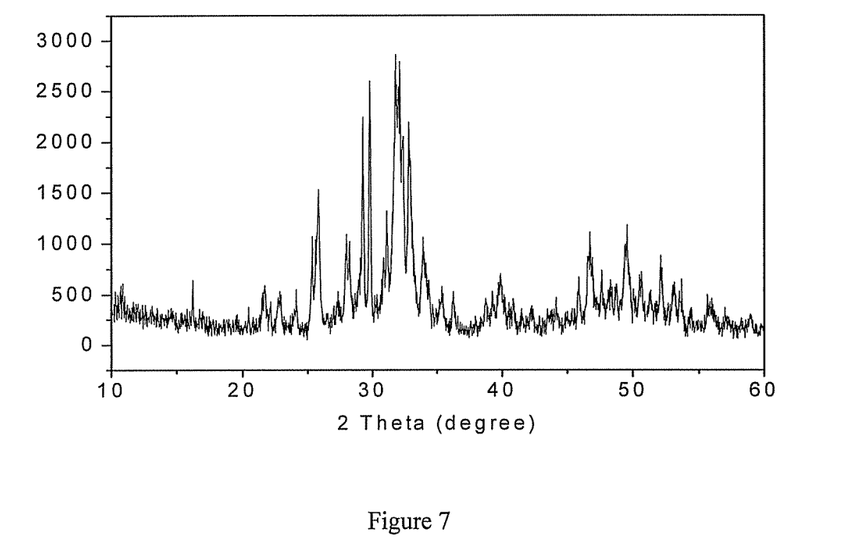
FIG. 7 is a XRD spectrum of the fluorapatite synthesized in the embodiment, disclosed in the present invention, of mixing tetracalcium phosphate, ammonium fluoride, and a phosphoric acid/water solution.
Figure 8:
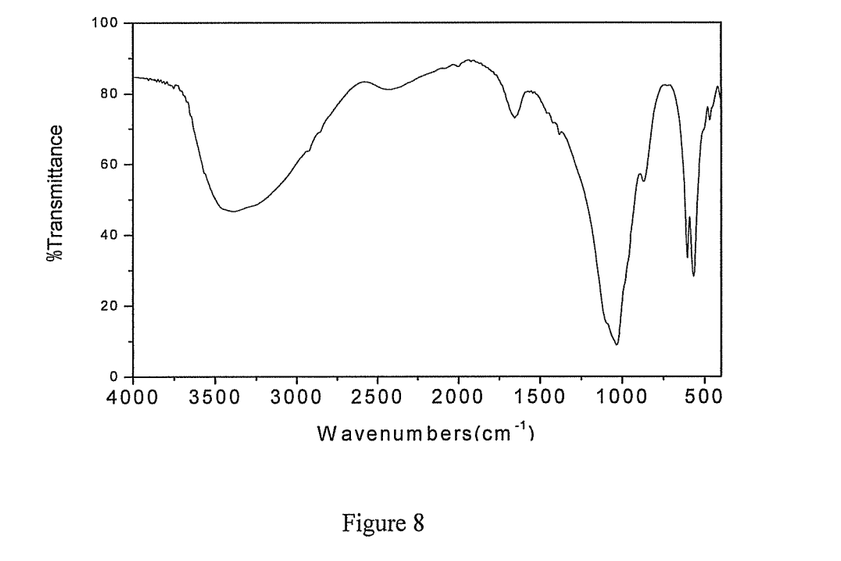
FIG. 8 is a IR spectrum of the fluorapatite synthesized in the embodiment, disclosed in the present invention, of mixing tetracalcium phosphate, ammonium fluoride, and a phosphoric acid/water solution.
Figure 9:
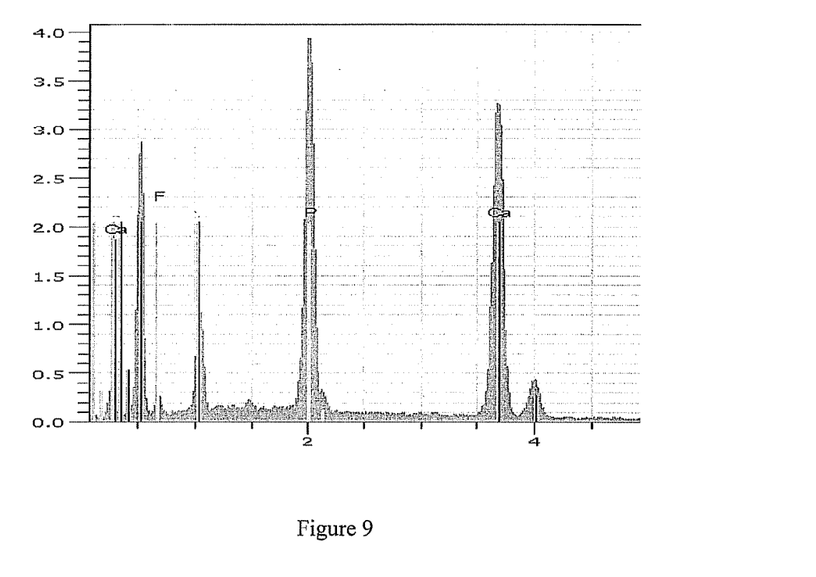
FIG. 9 is a EDS spectrum of the fluorapatite synthesized in the embodiment, disclosed in the present invention, of mixing tetracalcium phosphate, ammonium fluoride, and a phosphoric acid/water solution.

Tetracalcium phosphate (1.33 g) and ammonium fluoride (0.16 g) were mixed evenly, into which 0.196 g phosphoric acid and 4 mL water were then added. The obtained mixture was blent evenly by a key to form a cement-like substance in a mixing plate. The cement-like substance was kept in an environment with a temperature of 37° C. and a moisture of 100% for 3 days to form a material. The chemical structure and composition of this material were characterized by XRD, IR, and EDS, with the results shown in FIG. 7-9. According to the XRD spectrum, the resultant product has characteristic peaks near $2\theta=26°$, $2\theta=32°$, $2\theta=34°$, $2\theta=40°$, $2\theta=47°$, $2\theta=50°$, and this result indicates that the synthesized product is fluorapatite. According to the IR spectrum, the absorption peaks for $PO_4^{3-}$ appear at 1070 $cm^{-1}$ and 950 $cm^{-1}$, and the two absorption peaks at 1432 and 1750.8 $cm^{-1}$ and the absorption peaks between 2800 $cm^{-1}$ and 3472 $cm^{-1}$ all belong to hydroxyl group of water. The vibration peak of P—O—H bond of apatite appears at 877.7 $cm^{-1}$. According to the EDS spectrum, the synthesized product comprises elements of calcium, phosphorus, and fluorine, and a calculated quantitative result of atomic molar ratio is shown as follows: the atomic molar ratio of calcium to phosphorus is 1.67 and the atomic molar ratio of calcium to fluorine is 2. These results also demonstrate that the synthesized product is fluorapatite.

Example 5

Figure 10:
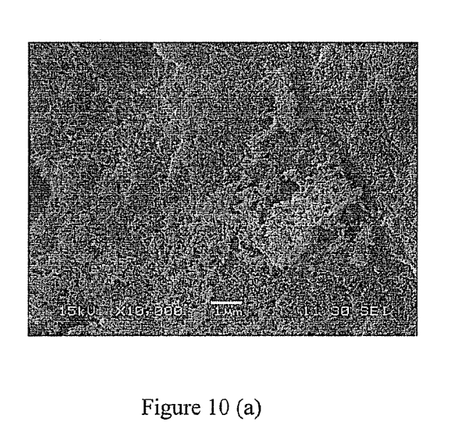
Figure 11A:
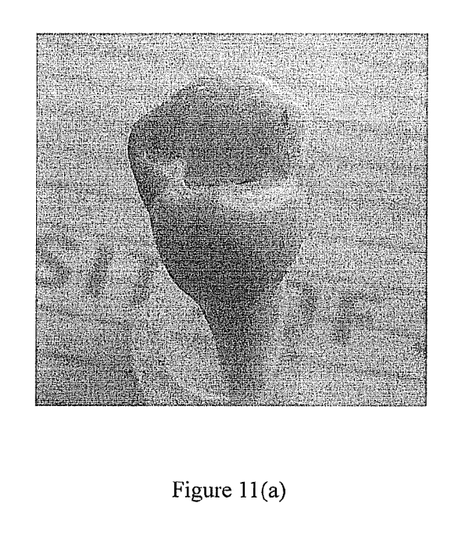
FIG. 11(a) is a photo of the tooth before repaired.
Figure 11B:
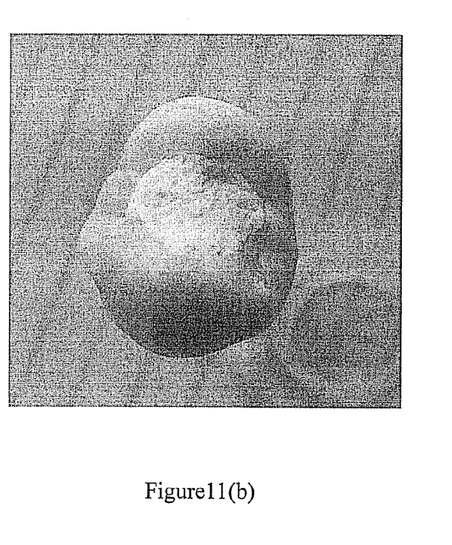
FIG. 11(b) is a photo of the tooth filled with the repairing material.
Figure 12:
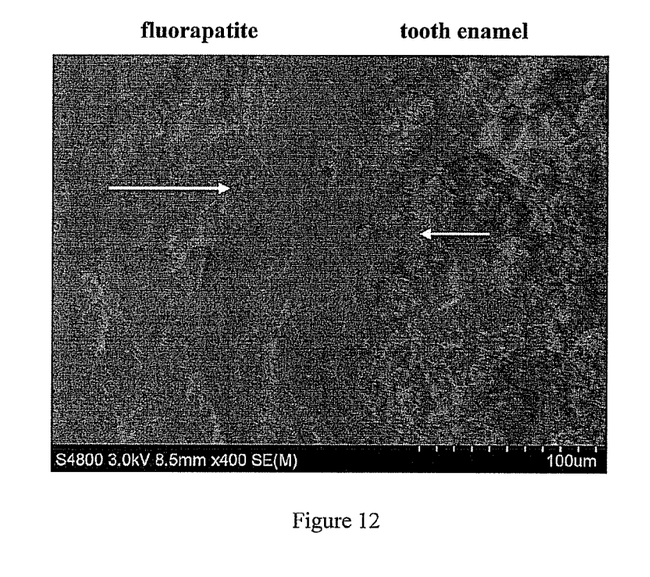
FIG. 12 is a SEM photo of repairing tooth enamel defects caused by caries with the fluorapatite synthesized in the embodiment, disclosed in the present invention, of mixing tetracalcium phosphate, ammonium fluoride, and a phosphoric acid/water solution, wherein the arrows point at the interface between fluorapatite and tooth enamel.

Tetracalcium phosphate (2.66 g) and ammonium fluoride (0.16 g) were mixed evenly, into which 0.196 g phosphoric acid and 4 mL water were then added. The obtained mixture was blent evenly by a key to form a cement-like substance in a mixing plate. An experimental sample was acquired after a tooth was filled with the cement-like substance in the place where tooth enamel defects caused by caries appeared and kept in an environment with a temperature of 37° C. and a moisture of 100% for 3 days. As shown in FIG. 10, microcosmic structure of the surface of the material was characterized by SEM. According to the SEM photo, fluorapatite was combined with tooth enamel closely without any obvious gap on their interface. This result also indicates that the repairing material fluorapatite has a similar composition with tooth enamel, so they can be easily combined together. The synthesized fluorapatite appeared as needle and bar like crystals that are combined together closely. The material and the combined tooth were cut through the center of the material, and the combining status of the interface between the material and the surface of tooth enamel defects was observed, as shown in FIG. 12.

Example 6

Tetracalcium phosphate (13.3 g) and ammonium fluoride (1.6 g) were mixed evenly, into which 1.96 g phosphoric acid and 6 mL water were then added. The mixture was blent evenly by a key to form a cement-like substance in a mixing plate. Fluorapatite was acquired after a tooth was filled with the cement-like substance in the place where enamel defects caused by caries appeared and kept in an environment with a temperature ranging from 35° C. to 38° C. and a moisture of 100% for 3 days.

Example 7

Tetracalcium phosphate (2.66 g), phosphoric acid (0.196 g), and 4 mL water were mixed evenly, then the mixture was blent by a key to form a cement-like substance. A solidified body was acquired after the cement-like substance was kept in an environment with a temperature of 37° C. and a moisture of 100% for 3 days. The solidified body was ground into powder, into which 0.16 g ammonium fluoride was added and mixed evenly, and then 4 mL water was added and mixed evenly. The obtained mixture was further blent by a key to form a cement-like substance. Fluorapatite was acquired after the cement-like substance was kept in an environment with a temperature ranging from 35° C. to 38° C. and a moisture of 100% for 3 days.

Example 8

Tetracalcium phosphate (1.33 g), phosphoric acid (0.098 g), and 2 mL water were mixed evenly, then the mixture was blent by a key to form a cement-like substance. A solidified body was acquired after the cement-like substance was kept in an environment with a temperature of 37° C. and a moisture of 100% for 3 days. The solidified body was ground into powder, into which 0.08 g ammonium fluoride was added and mixed evenly, and then 2 mL water was added and mixed evenly. The obtained mixture was further blent by a key to form a cement-like substance. Fluorapatite was acquired after a tooth was filled with the cement-like substance in the place where enamel defects caused by caries appeared and kept in an environment with a temperature ranging from 35° C. to 38° C. and a moisture of 100% for 3 days.

The examples of the present invention are intended to facilitate further understanding of the present invention, but those skilled in the art will recognize that any substitution and modification of the present invention is possible unless it deviates from the spirit and scope of the present invention and the Claims attached. Accordingly, the present invention should not be limited to the content disclosed by the Examples, and the scope claimed to be protected by the present invention is determined by the Claims attached.

The invention claimed is:

1. A method for producing fluorapatite, characterized in comprising:
   mixing tetracalcium phosphate, calcium hydrogen phosphate, and sodium fluoride to form a first mixture and then adding the first mixture into water, or mixing tetracalcium phosphate and ammonium fluoride to form a second mixture and then adding the second mixture into a phosphoric acid/water solution;
   blending the first mixture with water, or blending the second mixture with the phosphoric acid/water solution to form a mixed substance; and
   solidifying the mixed substance at a temperature of 35° C. to 38° C. and a moisture of 100% for 1-3 days.

2. The method of claim 1, characterized in that tetracalcium phosphate, calcium hydrogen phosphate, and sodium fluoride are used in an equal molar ratio and blended to form the mixed substance directly after being added into water.

3. The method of claim 2, characterized in that tetracalcium phosphate with a particle diameter of 1 to 20 μm and calcium hydrogen phosphate with a particle diameter of 1 to 20 μm are mixed evenly by a star-shape ball mill, blended with sodium fluoride, and then added to water.

4. The method of claim 3, characterized in that the ratio of the first mixture of tetracalcium phosphate, calcium hydrogen phosphate, and sodium fluoride to water is 1~4 (g/mL).

5. The method of claim 1, characterized in that tetracalcium phosphate and ammonium fluoride are mix and then added into the phosphoric acid/water solution to be blended to form the mixed substance, wherein the molar ratio of tetracalcium phosphate to phosphoric acid is 5:2 and tetracalcium phosphate and ammonium fluoride are used in an equal molar ratio.

6. The method of claim 5, characterized in that the percentage concentration of the phosphoric acid/water solution is 20%~70%.

7. The method of claim 1, characterized in that a solidified body is formed from tetracalcium phosphate and the phosphoric acid/water solution through a hydration reaction, and ground into powder, then the powder, ammonium fluoride, and water are blended to form the mixed substance.

8. The method of claim 7, characterized in that the concentration of the phosphoric acid/water solution is 20%~70%, and 1~4 gram of tetracalcium phosphate is added into each milliliter of the phosphoric acid/water solution.

9. The method of claim 8, characterized in that the molar ratio of tetracalcium phosphate to ammonium fluoride is 1:1.

10. A method of repairing enamel defects comprising applying the fluorapatite produced by the method of claim 1 to fill in the enamel defects.

11. A method of repairing enamel defects comprising applying the fluorapatite produced by the method of claim 2 to fill in the enamel defects.

12. A method of repairing enamel defects comprising applying the fluorapatite produced by the method of claim 3 to fill in the enamel defects.

13. A method of repairing enamel defects comprising applying the fluorapatite produced by the method of claim 4 to fill in the enamel defects.

14. A method of repairing enamel defects comprising applying the fluorapatite produced by the method of claim 5 to fill in the enamel defects.

15. A method of repairing enamel defects comprising applying the fluorapatite produced by the method of claim 6 to fill in the enamel defects.

16. A method of repairing enamel defects comprising applying the fluorapatite produced by the method of claim 7 to fill in the enamel defects.

17. A method of repairing enamel defects comprising applying the fluorapatite produced by the method of claim 8 to fill in the enamel defects.

18. A method of repairing enamel defects comprising applying the fluorapatite produced by the method of claim 9 to fill in the enamel defects.

19. The method of claim 1, wherein the solidifying step takes place at a location of a enamel defect.

20. The method of claim 19, wherein the enamel defect is caused by caries.

\* \* \* \* \*